US005181904A

United States Patent [19]

Cook et al.

[11] Patent Number: 5,181,904

[45] Date of Patent: Jan. 26, 1993

[54] PNEUMATIC TRACTION DEVICE WITH ELECTRICALLY CONTROLLED COMPRESSOR AND RELIEF VALVE

[76] Inventors: Gerry Cook, Box 1006, Sandpoint, Id. 83864; Gary Lusin, 340 E. Hollyhock, Belgrade, Mont. 59714

[21] Appl. No.: 261,353

[22] Filed: Oct. 24, 1988

[51] Int. Cl.[5] .......... A61F 5/00; A61H 1/02; A61H 7/00

[52] U.S. Cl. .......... 602/32; 602/35; 606/241

[58] Field of Search .......... 602/32, 35, 33; 606/237, 241, 242

[56] References Cited

U.S. PATENT DOCUMENTS

| | | | |
|---|---|---|---|
| 1,205,649 | 11/1916 | Miller | 128/71 |
| 2,773,499 | 12/1956 | Nieden | 128/75 |
| 2,910,061 | 10/1959 | Rabjohn | 128/75 |
| 3,086,518 | 4/1963 | Barlow et al. | 128/75 |
| 3,238,936 | 3/1966 | Siedentop | 128/71 |
| 3,734,088 | 5/1973 | Tucker | 128/71 |
| 3,847,146 | 11/1974 | Cushman | 128/75 |
| 3,888,243 | 6/1975 | Powlan | 128/75 |
| 3,937,216 | 2/1976 | Brown | 128/75 |
| 4,401,110 | 8/1983 | Ekholm | 128/70 |
| 4,466,427 | 8/1984 | Granberg | 128/75 |

FOREIGN PATENT DOCUMENTS

| | | | |
|---|---|---|---|
| 533297 | 2/1941 | Fed. Rep. of Germany | 128/203.11 |

*Primary Examiner*—Edgar S. Burr
*Assistant Examiner*—Kimberly L. Asher
*Attorney, Agent, or Firm*—Richard C. Conover

[57] ABSTRACT

A pneumatic traction device is provided which includes a pneumatic cylinder having a patient engaging device mounted to a pneumatic piston slidably positioned in the pneumatic cylinder. The pneumatic cylinder in turn is connected to a mounting device which can be mounted to a wall, for example. Compressed air, provided by a motor driven compressor, is directed on a timed basis to a chamber on one side of the pneumatic piston to move the pneumatic piston in a direction which pulls on the patient engaging device to provide traction to the patient. An electrically controllable relief valve is also provided by which the compressed air in the pneumatic cylinder can be bled into the atmosphere when the relief valve is opened. A controllable switch is provided for selectably controlling the operation of the compressor and relief valve.

4 Claims, 3 Drawing Sheets

PNEUMATIC TRACTION DEVICE WITH ELECTRICALLY CONTROLLED COMPRESSOR AND RELIEF VALVE

BACKGROUND OF THE INVENTION

The present invention relates to a pneumatic traction device for applying traction to a patient. Physical therapists have found it beneficial to apply traction to patients suffering from muscle and nerve injury. On many occasions, it is beneficial to provide traction on a periodic and repetitive basis so that a therapist may apply a greater amount of traction during any one cycle to achieve better results faster than would be the case if only a static force were used.

Static weight systems for applying traction to a patient are known such as shown in U.S. Pat. No. 4,508,109 to Saunders.

Apparatus for applying traction periodically is also known in the art. For example, see U.S. Pat. No. 3,786,803 to Petulla et al. This patent shows a direct drive traction device having a motor driven spool for spooling a cable connected to a harness attached to a patient. A controller is provided to activate the motor on a periodic basis to provide traction.

SUMMARY OF INVENTION

The present invention is directed to a pneumatic traction device which provides a simpler, more portable traction device than has heretofore been known. Further, the use of a pneumatic cylinder provides a beneficial advantage over static weight systems in that the pneumatic system provides a "soft" traction force on the patient by which better therapeutic results can be obtained. The present invention is portable and can be used in the patient's home as well as in a physical therapist's office. It is light weight, sturdy, and is not complicated to manufacture or use.

The present invention utilizes a pneumatic cylinder having a patient engaging device mounted to a pneumatic piston slidably positioned in a pneumatic cylinder. The pneumatic cylinder in turn is connected to a mounting device which can be mounted to a wall, for example. Compressed air, preferably provided by a motor driven compressor, is directed on a timed basis to a chamber on one side of the pneumatic piston to move the pneumatic piston in a direction which pulls on the patient engaging device to provide traction to the patient. Further, an electrically controllable relief valve is also provided by which the compressed air in the pneumatic cylinder can be bled into the atmosphere when the relief valve is opened. Control means are provided for selectably controlling the operation of the compressor and the relief valve. This control system can be as simple as a manual switch means which, in one position, manually turns on the compressor and closes the relief valve and, in the other position, opens the relief valve and turns off the compressor. The control means can also include a timer means for automatically providing the functions of the manual switch to traction to a patient on a periodic basis. Further, it is contemplated that the control circuit can be programmable with conventional means so that the amount of the force and also the time of the traction force can be selected by the user.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF PREFERRED EMBODIMENTS

Figure 1:
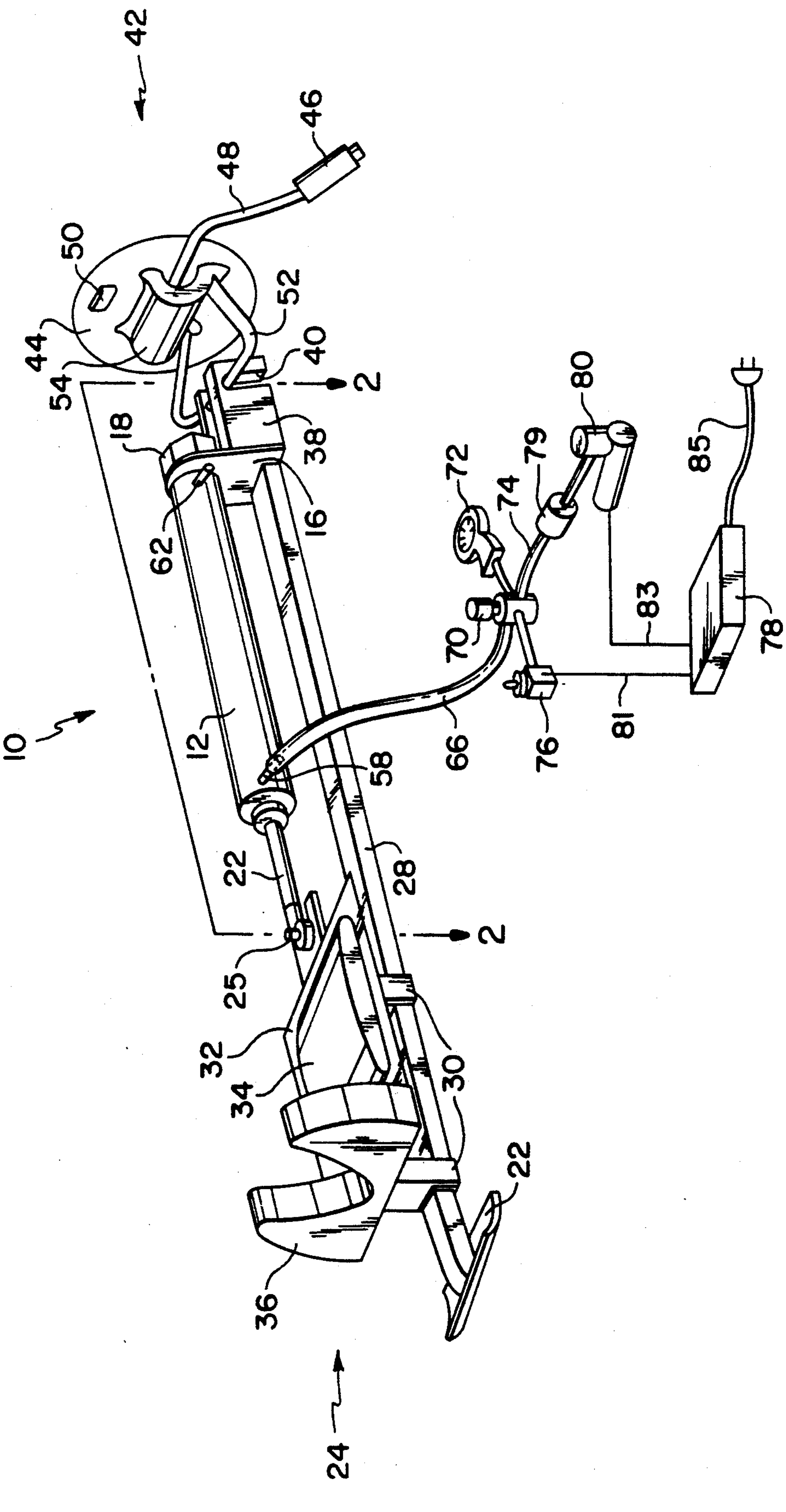
FIG. 1 is a perspective view of a pneumatic traction device according to the present invention.
Figure 2:
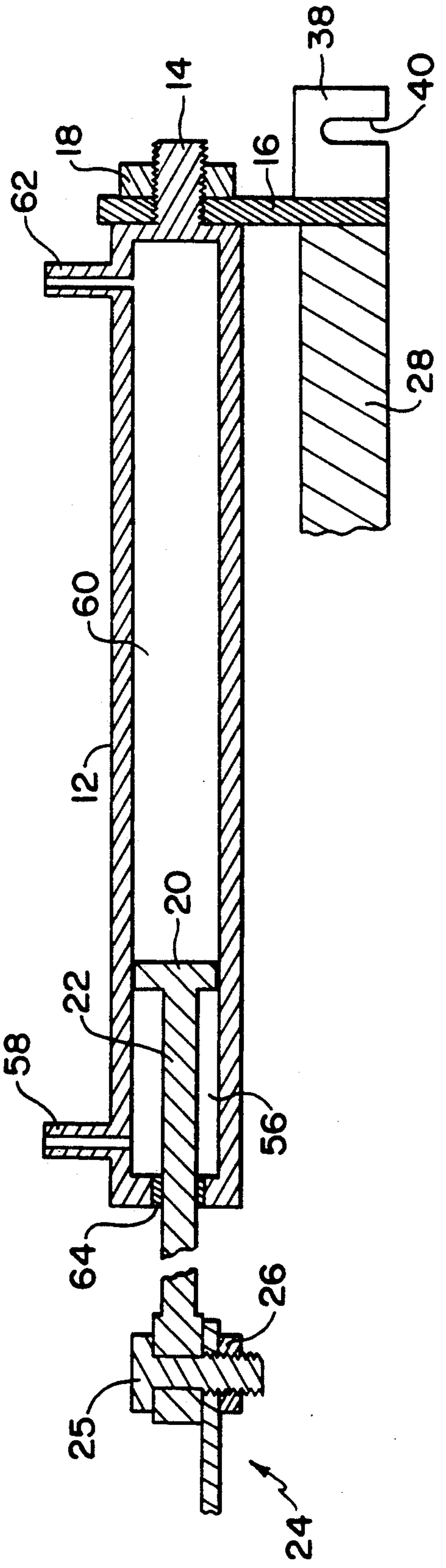
FIG. 2 is a cross-sectional view along line 2—2 in FIG. 1.

A pneumatic traction device 10 according to the present invention as shown in FIGS. 1 and 2. The device 10 as shown in FIG. 1 is used to provide cervical traction although it is intended that by substituting a different patient holding device, the traction device 10 could be used to provide traction for other body parts.

The device 10 includes a pneumatic cylinder 12 which at one end has an extending threaded shaft 14 which extends through a correspondingly sized hole in a bracket 16 which threaded shaft is received by a nut 18 to secure the pneumatic cylinder 12 to the bracket 16.

The pneumatic cylinder 12 encloses a pneumatic piston 20 as shown in FIG. 2. A shaft 22 is connected to the piston 20 again as shown in FIG. 2. The shaft 22 extends through a pressure seal 64 located in an end wall of cylinder 12 and is secured to a traction carriage device 24 with a bolt 25 and nut 26.

Bracket 16 is securely mounted to one end of a bar 28, which bar provides a framework for supporting pneumatic cylinder 12. The traction carriage device 24 includes a pair of slide pieces 30 slidably positioned on bar 28. When the shaft 22 moves the traction carriage device 24, the traction carriage device 24 slides on bar 28.

As shown in FIG. 1, the traction carriage device 24 includes a carriage base 32 which is secured to the slide pieces 30 as shown. In the embodiment shown in FIG. 1, the traction carriage device includes a headrest 34 mounted to the carriage base 32. Further a V-shaped cervical traction device 36 is mounted to the carriage base 32. The cervical traction device 36 is shaped to hold the back of a patient's skull approximate the occipital bone. Headrest 34 provides support for the patient's skull as cervical traction is applied. As above noted, the cervical traction device shown in FIG. 1 is illustrative of the use of the present invention although it is intended that this device may be used to place traction on other parts of the body by substituting a different traction carriage device 24.

In order to mount the pneumatic cylinder 12 to a wall, for example, a pair of mounting plates 38 are secured to bracket 16 as by welding as shown in FIGS. 1 and 2. These mounting plates 38 include a slot 40 for attaching the pneumatic traction device to a wall mounting device 42 as will be subsequently described.

The wall mounting device 42 as shown includes a suction disk 44. In a preferred embodiment, the wall mounting device is a Model JT156-RH Power-Grip, manufactured by Woods Power-Grip Co., Inc. The suction disk 44 may be placed on a smooth, flat or curved surface. A hand suction pump 46 evacuates air through a tube 48 thereby causing a suction force to be applied between the suction disk 44 and the surface. The suction can be readily released by pulling tab 50 in a manner well known in the art.

A mounting rod 52 is integrally formed with a mounting bracket assembly 54 securely mounted to suction disk 44. The rod 52 provides a means for connecting the pneumatic cylinder to the wall mounting device 42. The pneumatic cylinder 12 is connected to the wall mounting device 42 by placing the slot 40 over the rod 52 as shown in FIG. 1. It can be seen that when the slot 40 is inserted over the mounting rod 52 that the pneumatic cylinder 12 is rotatably secured to the wall surface.

The pneumatic cylinder 12 which slidably encloses piston 20 has a pair of internal chambers within the cylinder formed on either side of piston 20. Pressure chamber 56 on one side of piston 20 is fluidly connected to a source of compressed air through port 58 located in the chamber wall of chamber 56. Chamber 60 formed on the other side of piston 20 has a bleed post 62 which is located in the chamber wall and is in fluid communication with the atmosphere. The bleed port 62 insures that piston 20 can move freely within the chamber 60. When compressed air is forced into chamber 56, piston 20 moves toward chamber 60. This causes the traction carriage device 24 to also move to the right as shown in FIG. 1 and FIG. 2 causing traction on the patient.

A tube 66 connected to port 58 carries pressurized air to chamber 56. This tube 66 is connected to one port of a 4-port pressure regulator 70 as shown in FIG. 1. In a preferred embodiment, this pressure regulator is a Model No. R00R05 manufactured by Wilkenson Corporation. This regulator 70 has four ports, one of which is connected to tube 66 and a second of which is connected to a pressure gauge 72. A third port is connected to an air supply line 74. The fourth port is connected to a pressure relief valve 76 which is normally closed. In a preferred embodiment, the relief valve 76 is an MJV-3 manufactured by Clifford Co.

The air supply line 74 is connected to air compressor 80 through a one-way valve 79. The one-way valve 79 permits air to flow in the direction toward pneumatic cylinder 12 only.

An electrical control device 78 is provided to control the operation of air compressor 80 and relief valve 76. Control device 78 is electrically connected to relief valve 76 with wiring 81 and to compressor 80 with wiring 83. The control device 78 is constructed to close relief valve 76 when compressor 80 is on and to open relief valve 76 when compressor 80 is off.

Figure 3:
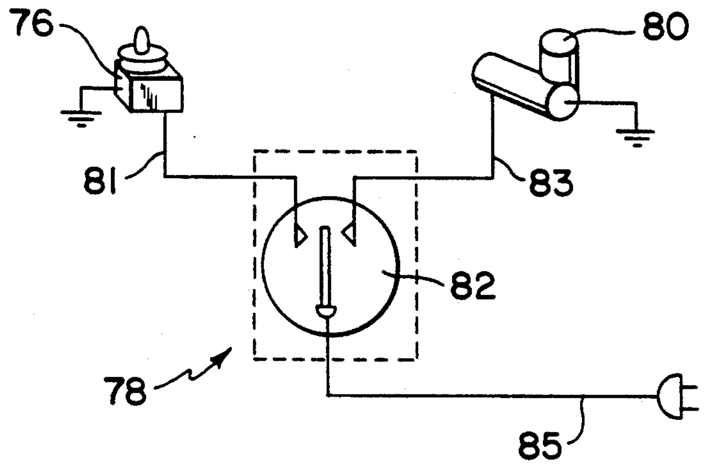
FIG. 3 is a schematic diagram of the control device included in FIG. 1 according to one embodiment of the present invention.

In one embodiment shown in FIG. 3, the control device 78 comprises a simple switch 82 which is connected to an electrical outlet with plug 85. When the switch 82 is manually switched to the relief valve 76 of the switch, the relief valve 76 is opened and the compressor 80 is turned off. On the other hand, when the switch is moved to the compressor 80 side of the switch, the compressor is turned on and the relief valve 76 is closed.

When the relief valve 76 is closed and air compressor 80 is turned on during the traction increment of a traction cycle, compressed air flows through air hose 66 to pressurize chamber 56 and places tractive force on carriage 24. During the rest increment of the traction cycle, the switch 82 is used to open relief valve 70 and turn the air compressor 80 off. By opening relief valve 70, chamber 56 is opened to the atmosphere thereby relaxing the tractive force pulling on carriage 24.

Figure 4:
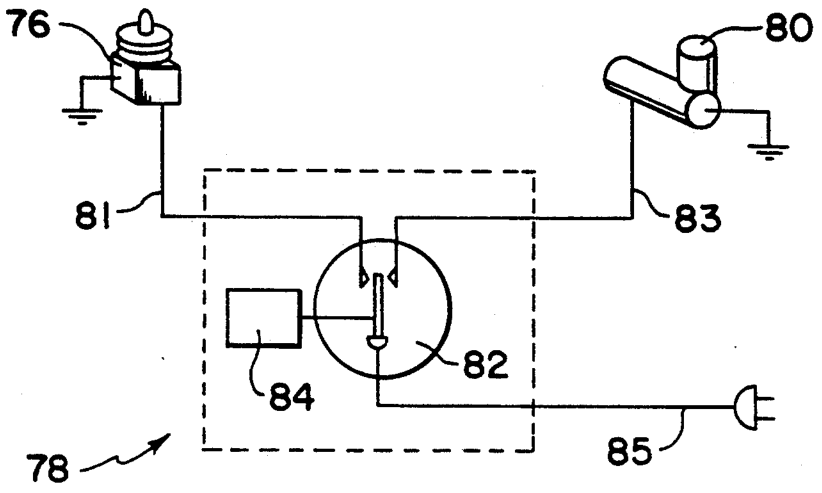
FIG. 4 is a schematic diagram of the control device included in FIG. 1 according to a second embodiment of the present invention.

A second embodiment of the present invention is shown in FIG. 4. In this embodiment, switch 82 is connected to a conventional cyclic timer 84 which may be set, for example, to provide a signal to turn the compressor on for 15 seconds and turn the compressor off for 45 seconds with the corresponding opening and closing of the relief valve 76. This provides an intermittent traction device which automatically sets the time of the periodic traction to be applied to a patient.

It is intended that the maximum traction pressure can be selected by manually adjusting the pressure regulator 70 to the desired pressure.

With the present invention, a light weight, sturdy traction device is provided which is portable and can be used as easily at home as well as in the physical therapist's office. It is versatile as it can be used to provide traction to many parts of the human body. It is a "soft" system which provides some tolerance in the traction process which is not otherwise available with direct drive systems now available in the marketplace.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims.

I claim:

1. A portable pneumatic traction device comprising:

a pneumatic cylinder enclosing a pneumatic piston:

a shaft having one end connected to the pneumatic piston;

a carriage traction device connected to the shaft at the other end thereof;

a surface mounting device for mounting an end of the pneumatic cylinder to a surface;

a controllable air compressor for supplying compressed air to a pressure chamber formed within the pneumatic cylinder on a side of the pneumatic piston;

a one-way valve connected between the air compressor and the pressure chamber for preventing airflow in the direction from the pressure chamber to the air compressor but allowing airflow from the air compressor to the pressure chamber;

a controllable relief valve connected to the pressure chamber within the pneumatic cylinder for releasing air from the chamber upon opening the relief valve;

electrical control means connected to both the controllable air compressor and the controllable relief valve whereupon when the air compressor is actuated, the pneumatic traction device applies a traction force to the carriage traction device and when the relief valve is opened, the traction force applied to the carriage traction device is relaxed.

2. A traction device according to claim 1 wherein the control means comprises a manual switch.

3. A traction device according to claim 1 wherein the control means comprises a switch which in turn is controlled by a timing device so that the air compressor can be turned on for a predetermined amount of time and then turned off for a predetermined amount of time.

4. A traction device according to claim 1 further including a pressure line connecting the air compressor and the pressure chamber;

a one-way valve means positioned in the pressure line for maintaining air in the pressure chamber when the controllable air compressor is off and the controllable relief valve is closed.

* * * * *